(12) United States Patent  
Amano et al.

(10) Patent No.: US 8,030,085 B2
(45) Date of Patent: Oct. 4, 2011

(54) METHOD FOR DISCRIMINATING BETWEEN PROSTATIC CANCER AND BENIGN PROSTATIC HYPERPLASIA

(75) Inventors: Junko Amano, Komae (JP); Kiyoko Hirano, Tokyo (JP); Ichiro Sugimoto, Nakama (JP)

(73) Assignee: The Noguchi Institute, Tokyo (JP)

( * ) Notice: Subject to any disclaimer, the term of this patent is extended or adjusted under 35 U.S.C. 154(b) by 208 days.

(21) Appl. No.: 12/216,202

(22) Filed: Jul. 1, 2008

(65) Prior Publication Data

US 2009/0023220 A1   Jan. 22, 2009

Related U.S. Application Data

(60) Provisional application No. 61/006,135, filed on Dec. 26, 2007.

(30) Foreign Application Priority Data

Jul. 6, 2007   (JP) .................................. 2007-178676

(51) Int. Cl.
*G01N 33/00* (2006.01)
*G01N 30/00* (2006.01)

(52) U.S. Cl. ............... 436/87; 436/64; 436/86; 436/171
(58) Field of Classification Search ............... 436/87, 436/64, 171, 86
See application file for complete search history.

(56) References Cited

U.S. PATENT DOCUMENTS

| 2004/0147033 A1* | 7/2004 | Shriver et al. ............... 436/87 |
| 2008/0071148 A1* | 3/2008 | Bosques et al. ............. 600/300 |
| 2008/0138908 A1* | 6/2008 | Amano ........................ 436/87 |

FOREIGN PATENT DOCUMENTS

| GB | 2 361 060 A1 | 10/2001 |
| JP | A-2000-514919 | 11/2000 |
| JP | A-2006-515927 | 6/2006 |
| WO | WO 98/00711 A1 | 1/1998 |
| WO | A-2002-055108 | 2/2002 |
| WO | WO 2004/060915 A2 | 7/2004 |
| WO | WO 2004/066808 A2 | 8/2004 |

OTHER PUBLICATIONS

Abstract of: Stamey et al., "Prostate-specific antigen as a serum marker for adenocarcinoma of the prostate," The New England Journal of Medicine, vol. 317, No. 15, pp. 909-916; 1987.

(Continued)

*Primary Examiner* — Vickie Kim
*Assistant Examiner* — Dwan A Gerido
(74) *Attorney, Agent, or Firm* — Oliff & Berridge, PLC

(57) ABSTRACT

The present invention provides a method for accurately discriminating between prostate carcinoma and benign prostatic hyperplasia based on a glycan structure of prostate specific antigen (PSA). The method of the present invention includes the steps of: purifying PSA from a sample derived from a subject; preparing a PSA derivative from the PSA; labeling the PSA derivative; and analyzing the labeled PSA derivative by the mass spectrometry method, in which the subject is identified as having prostate carcinoma when the ratio of the signal intensity of fucose-unbound glycan to the signal intensity of fucose-bound glycan in the labeled PSA derivative is greater than 1.0, and identified as having benign prostatic hyperplasia when the ratio is 1.0 or less.

3 Claims, 9 Drawing Sheets

OTHER PUBLICATIONS

Catalona et al., "Use of the Percentage of Free Prostate-Specific Antigen to Enhance Differentiation of Prostate Cancer from Benign Prostatic Disease: A Prospective Multicenter Clinical Trial," Journal of American Medical Association; vol. 279, No. 19, 1542-1547; 1998.

Sumi et al., "Serial lectin affinity chromatography demonstrates altered asparagine-linked sugar-chain structures of prostate-specific antigen in human prostate carcinoma," Journal Chromatography B, vol. 727, pp. 9-14; 1999.

Tabares et al., "Different glycan structures in prostate-specific antigen from prostate cancer sera in relation to seminal plasma PSA," Glycobiology; vol. 16, No. 2, pp. 132-145; 2006.

Peter et al., "Purification of Prostate-Specific Antigen from Human Serum by Indirect Immunosorption and Elution with a Hapten," Analytical Biochemistry, vol. 273, No. 1, pp. 98-104, 1999.

Kawinski et al., "Thiophilic Interaction Chromatography Facilitates Detection of Various Molecular Complexes of Prostate-Specific Antigen in Biological Fluids," The Prostate, vol. 50, No. 3, pp. 145-153, 2002.

Bindukumar et al., "Two step procedure for purification of enzymatically active prostate-specific antigen from semincal plasma," Journal of Chromatography B, vol. 813, No. 1-2, pp. 113-120, 2004.

Zhang et al., "Purification and Characterization of Different Molecular Forms of Prostate-Specific Antigen in Human Seminal Fluid," Clinical Chemistry., vol. 41, No. 11, pp. 1567-1573, 1995.

Okada et al., "Structural characteristics of the N-glycans of two isoforms of prostate-specific antigens purified from human seminal fluid," Biochimica ct Biophysica Acta, vol. 1525, No. 1-2, pp. 149-160, 2001.

Peracaula et al., "Altered glycosylation pattern allows the distinction between prostate-specific antigen (PSA) from normal and tumor origins," Glycobiology, vol. 13, No. 6, pp. 457-470, 2003.

Tajiri et al., "Oligosaccharide profiles of the prostate specific antigen in free and complexed forms from prostate cancer patient serum and in seminal plasma: a glycopeptide approach," Glycobiology Advance Access, pp. 1-20, Oct. 23, 2007.

Prakash S. et al., "Glycotyping of Prostate Specific Antigen," Oxford University Press, 2000, pp. 173-176, vol. 10 No. 2.

Jun. 9, 2010 European Search Report issued in EP 08 77 7915.

* cited by examiner

METHOD FOR DISCRIMINATING BETWEEN PROSTATIC CANCER AND BENIGN PROSTATIC HYPERPLASIA

CROSS-REFERENCE TO RELATED APPLICATIONS

This application claims the benefit of U.S. Provisional Patent Application No. 61/006,135 filed Dec. 26, 2007, and Japanese Patent Application No. 2007-178676, filed Jul. 6, 2007, which are hereby incorporated by reference herein in their entireties.

BACKGROUND OF THE INVENTION

1. Field of the Invention

The present invention relates to a novel method for discriminating between prostate carcinoma and benign prostatic hyperplasia. More specifically, the present invention relates to a novel method for discriminating between prostate carcinoma and benign prostatic hyperplasia based on the difference in glycan structure of prostate specific antigen (PSA).

2. Description of the Related Art

Prostate carcinoma (hereinafter, referred to as "PC") is one of the major causes of death in males. Prostate specific antigen (hereinafter, referred to as "PSA") has been recognized as the most important tumor marker for PC (for example, refer to Stamey et al., N. Engl. J. Med., 317, 909-916 (1987)). PSA is a glycoprotein having a molecular weight of approximately 30 kDa consisting of a protein portion consisting of 237 amino acid residues having a molecular weight of approximately 26 kDa, and a glycan portion linked to the amino acid residues (such as $Asn^{45}$) of the protein portion, or a derivative or analog thereof. The glycan portion represents approximately 8% of the molecular weight of PSA. Many documents have already described the usability of serum PSA test for the initial diagnosis of PC. However, there is a region between males affected with benign prostatic hyperplasia (hereinafter, referred to as "BPH") and males affected with PC, which is known as a gray zone, where it cannot discriminate between PC and BPH (for example, refer to Catalona et al., j. Am. Med. Assoc, 279, 1542-1547 (1998)). To solve the issue, several attempts have been made (such as discrimination based on PSA density, PSA gradient (annual increase rate) and the ratio of free PSA/total PSA). However, there is a significant overlap between the two lesions.

Recently, it has been reported that, in a study using the serial lectin affinity chromatography method using concanavalin A, phytohaemagglutinin E4 (PHA-E4) and PHA-L4, the structures of the glycans linked to asparagine (N) of PSA differ between the PC tissue and the BPH tissue (refer to Sumi et al., J. Chromatogr. B, 727, 9-14 (1994)). The report describes that the N-linked glycan in PSA is altered during the process of oncogenesis in the human prostate, and the N-linked glycan in PSA may serve as a diagnostic tool for PC.

As methods for detecting the PSA structure, several immunological approaches, using binding molecules which bind to a PSA glycan have been proposed. For example, a method for discriminating between PC and BPH has been reported, wherein the method brings PSA into contact with lectin, and measures PSA classified based on the affinity of PSA glycans to lectins (refer to Japanese Patent Laid-Open No. 2002-55108). In the report, it is described that the difference in the affinity of PSA glycans to lectin (Maackia amurensis lectin etc.) is based on the conformation of sialic acid at the glycan terminal. However, the specific structure of PSA glycan in subjects suffering from PC or BPH has not been determined.

Moreover, difference in fucose modification to PSA glycan is yet to be found between PC and BPH.

Moreover, there is reported a method for detecting PC based on whether at least a triantennary glycan is present in PSA (refer to Japanese Patent Application Laid-open No. 2000-514919). In the method, a binding molecule which binds to at least triantennary glycans, but not to monoantennary and biantennary glycans is used. The binding molecules which can be used include lectin (such as PHA-L) and antibodies.

As another approach, several reports have been made focusing on fucose in a PSA glycan. For example, a method has been proposed for measuring the fucose content in a PSA glycan, and diagnosing PC when the content is abnormally increased (refer to GB patent application publication No. 2361060).

Alternatively, a method has been proposed for evaluating the clinical condition of a subject by determining the glycan profile of the glycans in a target glycoprotein including PSA (refer to Japanese Patent Application Laid-open No. 2006-515927). The document describes that, in an analysis using the MALDI-MS method, the PSA glycan in subjects suffering from PC has a different fucosylated structure from that of the normal PSA glycan. However, it does not describe the specific structure of PSA glycan in the subjects-suffering from PC.

Moreover, there has been made a report focusing on the content of fucose-bound glycan and fucose-unbound glycan in PSA (refer to Tabares et al., Glycobiology, 16(2), 132-145 (2006)). In the report, they analyzed the structures of PSA glycans only in one subject having a significantly high serum PSA concentration (1.8 µg/mL) by HPLC, and it describes that the ratio of the content of fucose-unbound glycan to fucose-bound glycan was 5.25 (84/16). On the other hand, there has been reported an analysis of glycopeptides prepared from serum PSA of two subjects suffering from PC having a further high serum PSA concentration (10 µg/mL or more) by MALDI-QIT-TOF MS (refer to Tajiri et al., Glycobiology Advance Access published Oct. 23, 2007 http://glycob.oxfordjournals.org/cgi/reprint/cwm117v1). The study discloses that the content of fucose-bound glycan is 100% and 64% respectively, and that the fucose-bound glycans are more abundant compared with the fucose-unbound glycans.

However, the structures of PSA glycans in subjects suffering from BPH is yet to be revealed, and discrimination between BPH and PC based on the specific structures of PSA glycans has not been performed.

SUMMARY OF THE INVENTION

Therefore, the problem to be solved by the present invention is to provide a method for accurately discriminating between BPH and PC based on glycan structures of PSA by determining the specific structure of PSA glycan in a subject suffering from BPH or PC.

The method for discriminating between PC and BPH according to the present invention comprises the steps of: (1) purifying PSA from a sample derived from a subject; (2) preparing a PSA derivative from the PSA purified in Step (1); (3) labeling the PSA derivative obtained in Step (2); and (4) analyzing the labeled PSA derivative obtained in Step (3) by the mass spectrometry method, wherein the subject is identified as having prostate carcinoma when the ratio of the signal intensity of fucose-unbound glycan to the signal intensity of fucose-bound glycan in the labeled PSA derivative is greater than 1.0, and identified as having benign prostatic hyperplasia when the ratio is 1.0 or less. In the method, the PSA derivative prepared in Step (2) may be a glycan or glycopeptide derived from PSA.

By taking the above steps, PC and BPH can be discriminated with high accuracy even in subjects having almost the same level of PSA concentration in sera by measuring the signal intensity ratio R of fucose-unbound glycan/fucose-bound glycan in the PSA glycans. Moreover, in both PC and BPH, the signal intensity ratio R of fucose-unbound glycan/fucose-bound glycan has no correlation with serum PSA concentration, and R is greater than 1.0 in PC and R is 1.0 or less in BPH.

Therefore, for subjects who have shown a high PSA level (4 ng/mL or more) in the method measuring PSA concentration in serum, which is frequently used in the current PC screening, and undergone a painful second test, a needle biopsy, unnecessary tests can be avoided by applying the present invention. Moreover, it is known that PSA concentration in serum increases with age. Therefore, in particular, discriminating between PC and BPH by the method of the present invention with high accuracy not only contributes to medicine but also exerts a favorable effect on medical economics in an aging society.

Further features of the present invention will become apparent from the following description of exemplary embodiments (with reference to the attached drawings).

DESCRIPTION OF THE EMBODIMENTS

Figure 1:
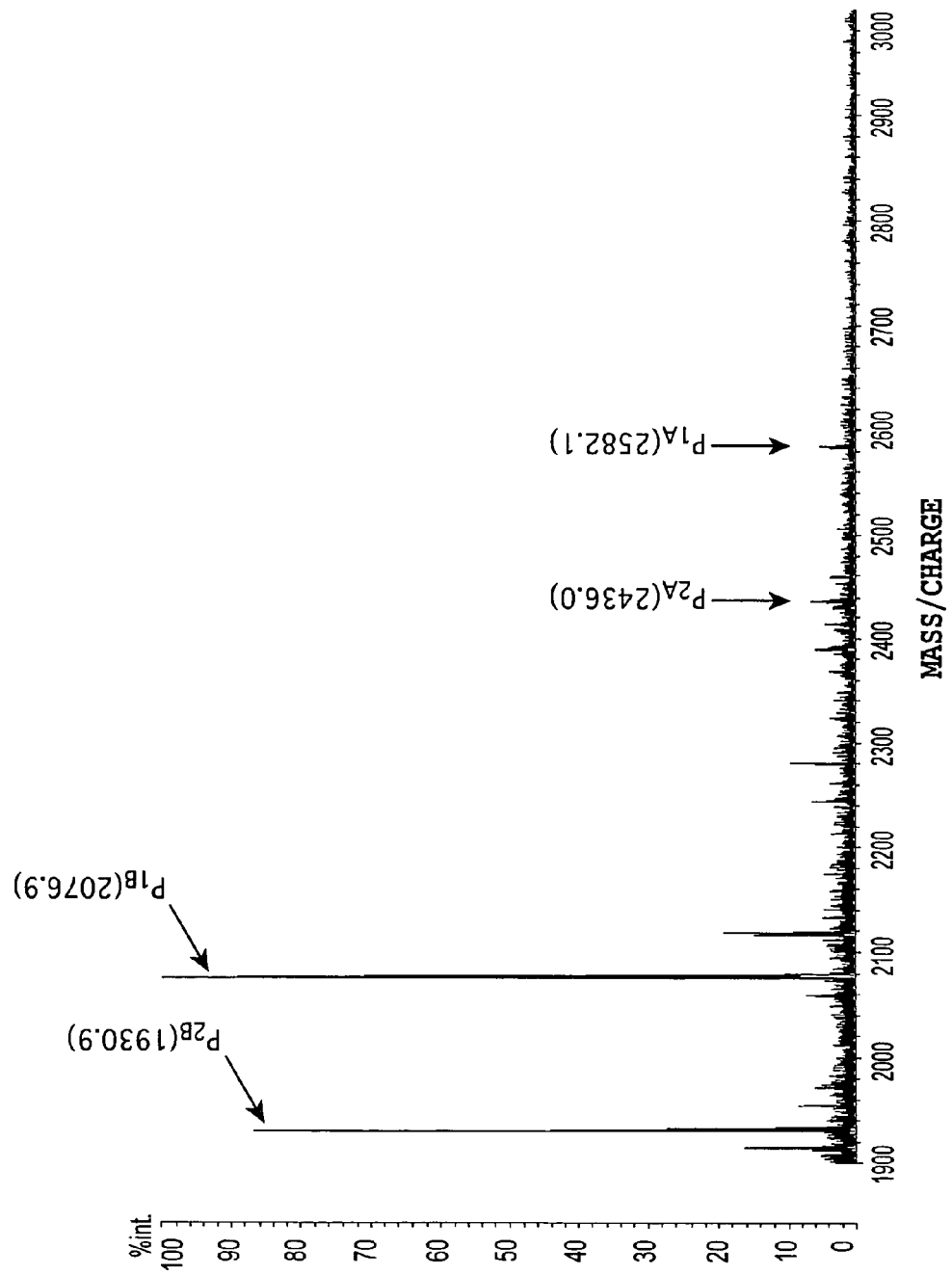
FIG. 1 is a diagram showing the negative ion MS spectrum obtained in Example 1.

The method for discriminating between PC and BPH according to the present invention comprises the steps of: (1) purifying PSA from a sample derived from a subject; (2) preparing a PSA derivative from the PSA purified in Step (1); (3) labeling the PSA derivative obtained in Step (2); and (4) analyzing the labeled PSA derivative obtained in Step (3) by the mass spectrometry method, wherein the subject is identified as having prostate carcinoma when the ratio of the signal intensity of fucose-unbound glycan to the signal intensity of fucose-bound glycan in the labeled PSA derivative is greater than 1.0, and identified as having benign prostatic hyperplasia when the ratio is 1.0 or less.

In Step (1), PSA is purified from a sample derived from a subject. The sample derived from a subject used in Step (1) include body fluid such as blood (including serum and plasma), urine and semen (seminal plasma) and prostate cells. Preferably, the sample is serum. Step (1) can be performed by any of methods known in the art.

For example, when serum derived from a subject is used as a sample in Step (1), PSA purification can be performed by using the immunoprecipitation method by means of magnetic beads (refer to Peter et al., Anal. Biochem., 273(1), 98-104 (1999)). For example, (a) antibody magnetic beads are prepared by binding a biotinylated digoxigenin antibody to streptavidin-coated magnetic beads, (b) the digoxigenin-labeled PSA antibody is added to the antibody magnetic beads, and incubation is performed, and (c) serum derived from a subject is added, and immunoprecipitation is performed. Then, digoxigenin-lysine hydrochloride is added to elute the compounds bound to the precipitated antibody magnetic beads and, subsequently, PSA is separated by using the sodium dodecylsulfate-polyacrylamide gel electrophoresis method (SDS-PAGE) to obtain peptides derived from PSA. According to the above described document, in order to perform an analysis of the obtained peptides derived from PSA by the MALDI-MS method, approximately 7.6 µg of PSA was required in the sample derived from the subject.

Alternatively, when serum derived from a subject is used as a sample in Step (1), a method which combines several kinds of affinity chromatography can be used. For example, on serum derived from a subject, affinity chromatography based on sulfurphilic adsorption (Fractogel (registered trademark) EMD TA), affinity chromatography (Cibacron Blue 3GA), affinity chromatography (Protein A Sepharose CL-4B) and affinity chromatography (HiTrap heparin column HPLC) are performed (refer to Tabares et al., Glycobiology, 16(2), 132-145 (2006)). The obtained eluate is processed with ethanolamine to obtain free PSA. The free PSA is treated by the above described immunoprecipitation method to obtain a PSA derivative. According to the above described document, in order to perform an analysis of the obtained PSA derivative, approximately 63 µg of PSA was required in the sample derived from the subject.

Furthermore, when serum derived from a subject is used as a sample in Step (1), PSA purification can be performed by using affinity chromatography based on sulfurphilic adsorption in a single step (refer to Kawinski et. al., Prostate, 50(3): 145-153 (2002)). For example, PSA, which is derived from human semen, serum of a patient with prostate carcinoma and a supernatant of culture medium of prostate carcinoma cells (LNCaP), is purified by chromatography using 3S, T-gel slurry (Fractogel (registered trademark) EMD TA), and one can identify its free form or complex state with α1-antichymotrypsin (ACT) and the like by using the Western blot method. Alternatively, when semen derived from a subject is used as a sample, PSA can be purified by combining affinity chromatography based on sulfurphilic adsorption and gel filtration (refer to Bindukumar et al., J. Chromatogr. B, Analyt. Technol. Biomed. Life. Sci., 813(1-2), 113-120 (2004)). For example, one can combine affinity chromatography based on sulfurphilic adsorption (Fractogel (registered trademark) TA 650 (S)) and gel filtration (Ultrogel AcA-54). By the combined method, free PSA could be collected at 72% yield.

Alternatively, when semen derived from a subject is used as a sample in Step (1), PSA purification can be performed by the following method (refer to Zhang et al., Clin. Chem., 41(11), 1567-1573 (1995) and Okada et al., Biochim. Biophys. Acta, 1525(1-2), 149-160 (2001)). For example, PSA can be purified by sequentially performing precipitation by addition of ammonium sulfate, hydrophobic interaction chromatography (Phenyl-Sepharose-HP column), gel filtration (Sephacryl S-200 column) and anion exchange chromatography (Resourse Q column). In the method, it has been reported that the final recovery rate of PSA was 30.1% when 33.9 mg of PSA was included in the sample.

Furthermore, when androgen-dependent LNCaP derived from the subject is used as a sample in Step (1), PSA can be purified by a method which combines ultra filtration and various kinds of chromatography (refer to Peracaula et al., Glycobiology, 13(6), 457-470 (2003)). For example, PSA can be purified by sequentially performing ultra filtration of culture medium containing LNCaP cultured by an appropriate method (5 kDa cut-off polysulfone membrane (Millipore Corp.)), affinity chromatography (Cibacron Blue 3GA), gel filtration (Biogel P60), affinity chromatography (Cibacron Blue 3GA) and reversed phase chromatography (using 214TP-RP C4, HPLC).

Next, a PSA derivative is prepared from the purified PSA in Step (2). In the present invention, a "PSA derivative" refers to a glycan and glycopeptide separated from PSA. For example, PSA can be treated with an endoprotease (such as thermolysin, endoproteinase Arg-C, endoproteinase Lys-C, trypsin, chymotrypsin, pepsin, proline-specific endopeptidase, protease V8, proteinase K, aminopeptidase M and carboxypeptidase B) or peptide bond cleaving agents to form a glycopeptide, and the glycopeptide can be used in Step (3).

In another method, PSA can be enzymically treated to form free glycans. Alternatively, the above described glycopeptides derived from PSA can be enzymically treated to form free glycans. The glycans obtained in the above method can be used in Step (3). In the enzymatic treatment, for example, peptide N-glycanase (PNGase F and PNGase A), endoglycosidase (EndoH and EndoF) and/or one or more proteases (such as trypsin and endoproteinase Lys-C) can be used. Alternatively, PSA or the glycopeptides derived from PSA can be treated by chemical means (such as degradation by anhydrous hydrazine and reductive or non-reductive β-elimination) to form free glycans. The glycans obtained in the above method can be used in the following Step (3). Moreover, it is possible to use glycans and glycopeptides, in which sialic acid is removed by performing sialidase treatment or acid hydrolysis.

Moreover, when electrophoresis is performed at the final stage of Step (1) to cut out the PSA band, the band cut out can be treated with the above described reactant to perform the digestion in the gel in order to generate glycopeptides and/or glycans.

The PSA derivative is labeled in Step (3). As a labeling compound, a compound having a fused polycyclic hydrocarbon portion such as naphthalene, anthracene and pyrene, a reactive functional group which can bind to the molecule to be analyzed, and an optional spacer portion linking the fused polycyclic hydrocarbon portion and the reactive functional group can be used. The fused polycyclic hydrocarbon portion is preferably pyrene. The reactive functional group has reactivity with the carboxy group of sialic acid or the reducing terminal of saccharide, and includes, for example, diazomethyl group, amino group and hydrazide group. The spacer portion includes, for example, the linear or branched alkylene group. The labeling compounds which can be used in the present invention include 1-pyrenyl diazomethane (PDAM), 1-pyrenebutanoic acid hydrazide (PBH), 1-pyreneacetic acid hydrazide, 1-pyrenepropionic acid hydrazide, aminopyrene (including constitutional isomers thereof), 1-pyrenemethylamine, 1-pyrenepropylamine and 1-pyrenebutylaimine. The most preferably used labeling compound is PDAM.

Step (3) can be performed by mixing the PSA derivative and the labeling compound, and heating. Heating can be performed, for example, at a temperature in the range of 40 to 50° C. Optionally, labeling can be performed in the presence of accelerator such as water soluble carbodiimide or N-hydroxysuccinimide. More preferably, labeling can be performed by dripping a solution of the PSA derivative on a target plate being used in the MALDI method and letting it to dry, and dripping a solution of the labeling compound thereto and heating it to dry.

The labeled PSA derivative is analyzed by the mass spectrometry method (MS) in Step (4). The ionization part which can be used in MS includes a matrix-assisted laser desorption ionization (MALDI) type apparatus or an electrospray ionization (ESI) type apparatus. In the present invention, ionization efficiency of the labeled PSA derivative in the MALDI method is improved by binding a fused polycyclic hydrocarbon group such as pyrene, in comparison with an unlabeled PSA derivative. Moreover, it is easier to apply the ESI method to the labeled PSA derivative of the present invention. This is because the labeled PSA derivative of the present invention is soluble to organic solvents by introducing a fused polycyclic hydrocarbon group, in comparison with the PSA derivative, which has high hydrophilicity and is hard to obtain an organic solution of a sample to be used in the ESI method.

The separation part which can be used in MS includes any of apparatuses known in the art such as time-of-flight type (TOF type), double-focusing type and quadrupole-focusing type. In particular, it is convenient to use an apparatus having an ion trap, considering the fact that one performs an $MS^n$ ($n \geq 2$) analysis. A particularly preferred apparatus is a quadrupole-focusing ion trap-time-of-flight type (QIT-TOF). In the method, any one of linear type, reflectron type and multi-turn type can be used as a time-of-flight type apparatus.

Next, in the obtained MS spectrum, a pair of peaks $P_1$ and $P_2$, whose molecular weights differ by 146 Da, which corresponds to the presence or absence of fucose, is chosen. Used herein, $P_1$ represents a peak of a larger molecular weight, corresponding to fucose-bound glycans, and $P_2$ represents a peak of a smaller molecular weight, corresponding to fucose-unbound glycans. Subsequently, signal intensities of the peaks corresponding to fucose-bound glycans $S(P_1)$ and fucose-unbound glycans $S(P_2)$ are measured, and the ratio $R=S(P_2)/S(P_1)$ is calculated. When the obtained R is greater than 1, the subject is identified as affected with PC, and when the obtained R is 1 or less, the subject is identified as affected with BPH. In the MS spectrum obtained by the present step, plural pairs of peaks whose molecular weights differ by 146 Da can be chosen to perform the above described discrimination procedure. Alternatively, a pair of peaks whose molecular weights differ by 146 Da can be chosen among the peaks, in which the labeling compound and/or the sialic acid residue and the like are eliminated in the mass spectrometer, to perform the above described discrimination procedure.

EXAMPLES

Example 1

(a) Step 1 Isolation of PSA

First, immunoglobulin in serum was removed. A disposable plastic column (Pierce Biotechnology, Inc.) was filled with 4 mL of Protein A agarose (Pierce Biotechnology, Inc.), and equilibrated by using phosphate buffered saline (PBS). A mixture of serum of a subject who has been diagnosed with BPH (T-13) and PBS was added to the Protein A agarose-filled column, and the column was rinsed with two column volume (CV) of PBS. A fraction containing PSA which was not bound to the carrier was collected, and $Na_2SO_4$ was added to a final concentration of 1 M.

Next, albumin, which is a major protein in serum, was removed. A disposable plastic column was filled with 1 mL of Fractogel (trademark) EMD TA(S) (Merck KGaA), and equilibrated with 20 mM phosphate buffer (pH 7.4, containing $Na_2SO_4$ (1 M)). The above described fraction containing PSA was added to the Fractogel-filled column, and the column was rinsed with 7 CV of the same buffer by using a liquid feed pump. Next, the adsorbed protein was eluted with 20 mM phosphate buffer (pH 7.4, not containing $Na_2SO_4$) to obtain a fraction containing PSA.

Next, PSA was released from the complex of PSA and $\alpha_1$-antichymotrypsin (PSA-ACT) in serum. An equal volume of 4 M ethanolamine solution (pH 10.5) was added to the above described fraction containing PSA to a final concentration of 2 M ethanolamine. The mixture was then shaken for 14 hours at 25° C. for reaction. Subsequently, 2 M hydrochloric acid was added to the reaction mixture while cooling in an ice bath to neutralize the reaction mixture.

Next, immunoprecipitation using a PSA antibody was performed. First, a commercially available anti-human PSA rabbit polyclonal antibody (manufactured by DAKO Inc.) was bound to Dynabeads (registered trademark) Protein G (Invitrogen Corp.). Subsequently, by using dimethyl pimelimidate (DMP, Pierce Biotechnology, Inc.), the antibody and the magnetic beads were crosslinked to obtain antibody magnetic beads. The PSA antibody magnetic beads were added to the above described neutralized reaction mixture, and the mixture was shaken for 1 hour at 4° C. Subsequently, the PSA antibody magnetic beads were rinsed three times with PBS containing 0.02% Tween-20 and once with PBS. Furthermore, 1 M propionic acid was added to the PSA antibody magnetic beads, and the mixture was shaken for 40 minutes at 4° C. to elute and collect the protein adsorbed to the PSA antibody magnetic beads. The eluted protein was dried on a centrifugal concentrator (SpeedVac).

As a result of analyzing the dried protein by the Enzyme-linked immunosorbent assay method (ELISA, Eiken Chemical Co., Ltd.) and electrophoresis, it was revealed that approximately 50% of PSA contained in the initial serum was collected. The above process can be completed within 2 days and, therefore, is a simple and rapid process with high yield.

To 0.125 M Tris-HCl buffer (pH 6.8), 10% mercaptoethanol, 4% SDS, 10% sucrose and 0.004% bromophenol blue were added to prepare a sample buffer. To 20 μL of the sample buffer, the purified PSA in step 1 was added, and the mixture was heated to 100° C. for 3 minutes and then cooled by leaving it to stand in an ice bath. The obtained sample was separated by electrophoresis on a 10% polyacrylamide gel. After separation by electrophoresis, the polyacrylamide gel was gently rinsed with purified water. Subsequently, staining by SYPRO (registered trademark) Ruby (Invitrogen Corp.) was performed. A gel containing the stained protein was cut out and transferred to a 1.5 mL tube. The gel cut out was sequentially rinsed by using purified water, an aqueous solution of 50% acetonitrile and acetonitrile, and the gel was then dried.

Moreover, separately, when the above described procedure was repeated by using 1 mL of serum having PSA concentration in the range of 4 to 10 ng/mL, a strong PSA band was observed in Western blot. From this result, it was proven that PSA at low concentrations such as this can be efficiently purified by the above described method.

(b) Step 2 Preparation of Glycans (a PSA Derivative)

To a tube containing the dried gel obtained in Step (a), an aqueous solution containing 10 mM dithiothreitol (DTT) and 25 mM ammonium bicarbonate (pH 8.0) was added. The mixture was shaken for 1 hour at 56° C. under light-shielded conditions to perform a reduction reaction, and the solution in the tube was removed. An aqueous solution containing 55 mM iodoacetamide was added to the tube, and the mixture was shaken for 45 minutes at room temperature under light-shielded conditions to perform an alkylation reaction, and the solution in the tube was removed. The gel which was subjected to reduction and alkylation was rinsed with an aqueous solution of 25 mM ammonium bicarbonate (pH 8.0) and acetonitrile, and the gel was then dried.

To the gel obtained by the above described method, Lysyl Endopeptidase (registered trademark) solution (250 ng, Wako Pure Chemical Industries, Ltd. (mass spectrometry grade)) and an aqueous solution of 25 mM ammonium bicarbonate (pH 8.0) were added, and the mixture was left to stand in ice for 45 minutes to swell the gel. Subsequently, the reaction mixture was gently agitated for 18 hours at 37° C. After adding an aqueous solution of 75% acetonitrile (containing 0.1% trifluoroacetic acid), the mixture was shaken for 20 minutes to perform extraction, and the solution was collected.

The collected solution was dried on a centrifugal concentrator. To the residue, an aqueous solution of 50 mM ammonium bicarbonate (pH 8.0) containing 1 μg of Pefabloc SC (Roche Diagnostics K.K.) was added and, subsequently, 1 unit (1 unit/μL) of peptide N-glycosidase F (SIGMA-ALDRICH Corp.) was added. The mixture was then shaken for 18 hours at 37° C. After shaking, 1 μL of an aqueous solution of 1% trifluoroacetic acid was added to the reaction mixture. By using a C18 chip filled with octadecyl (C18) silica carrier, suction and ejection of the reaction mixture were repeated. As a result, the peptides were adsorbed and separated from glycans in the reaction mixture, and a glycan fraction was obtained. Subsequently, by using an aqueous solution of 70% acetonitrile 0.1% trifluoroacetic acid, the peptides were eluted from the C18 chip to obtain a peptide fraction. Peptides derived from PSA were detected from the obtained peptide fraction.

A microspin column was filled with 30 mg of carbon graphite (GL Sciences Inc.) and rinsed. To the graphite-filled microspin column, the glycan fraction was added, and an aqueous solution of 5% acetonitrile (0.1% trifluoroacetic acid) was further added as a rinsing solution. The mixture was rinsed by centrifugation (300×g, for 1 to 2 minutes). After removing the rinsing solution, an aqueous solution of 50% acetonitrile (0.1% trifluoroacetic acid) was added to perform centrifugation (300×g, for 1 to 2 minutes) to elute the glycans, and the glycan eluate was obtained. The collected glycan eluate was dried on a centrifugal concentrator, and redissolved in 2 μL of purified water to obtain a glycan solution.

(c) Step 3 Labeling of Glycans (a PSA Derivative)

On a target plate for MALDI, 0.5 μL of the glycan solution obtained in step 2 was dripped and dried in the air. Next, on that place of the target plate, 0.25 μL of a DMSO solution of 1-pyrenyl diazomethane (PDAM, 500 pmol) was dripped, heated for approximately 25 minutes to 40° C., and dried. By the procedure, glycans labeled with PDAM were obtained on the target plate.

(d) Step 4 MS Analysis

To the target plate carrying the labeled glycans obtained in step 3, 0.5 μL of 50% acetonitrile solution of 2,5-dihydroxybenzoic acid (DHBA) (concentration 10 mg/mL) was dripped, and dried at room temperature.

The obtained target plate was set at a MALDI-QIT-TOFMS apparatus, the AXIMA-QIT (manufactured by Shimadzu Corporation/Kratos Analytical Ltd.), and an MS analysis was performed. In order to perform a quantitative comparison, the region surrounded by an outer boundary larger than the spread of the sample on the target plate was raster scanned, and all of the significant signals were accumulated. FIG. 1 shows a representative example of the obtained MS spectrum.

As a result of separately performing an $MS^2$ analysis using various ions as precursor ions, it was revealed that the peak $P_{1A}$ of m/z=2582 in FIG. 1 corresponds to fucose-bound glycan shown in Formula A, and the peak $P_{2A}$ of m/z=2436 in FIG. 1 corresponds to fucose-unbound glycan shown in Formula B. Here, "Pyrene" in the formulae represents the pyrene-labeled portion (1-pyrenylmethyl group) derived from PDAM, and the open brace represents that the substructure shown to the left is bound to either one of the substructures shown to the right. Moreover, in the formulae, Neu5Ac represents N-acetylneuraminic acid, Gal represents galactose, GlcNAc represents N-acetylglucosamine, Fuc represents fucose and Man represents mannose.

Signal intensities of the peaks $P_{1A}$ and $P_{2A}$, $S(P_{1A})$ and $S(P_{2A})$, were measured, and the ratio $R=S(P_{2A})/S(P_{1A})$ was calculated. The value was obtained as R=0.69.

sponding to a structure in which Fuc-GlcNAc is released, was detected, the peak of m/z=1856, corresponding to a structure in which only GlcNAc is released, could not be detected. Therefore, it was found that fucose was bound to GlcNAc at the reducing terminal. Moreover, in the spectrum of FIG. 2, the peak of m/z=655, which corresponds to Neu5Ac-Gal-GlcNAc, and the peak of m/z=817, which corresponds to Neu5Ac-Gal-GlcNAc-Man, and the like were detected. Therefore, it was found that N-acetylneuraminic acid was bound to the non-reducing terminal. Moreover, since the peak of m/z=961, which corresponds to Neu5Ac-Gal-GlcNAc-Man-Man, which is ion D, was detected, it was revealed that there is an isomer, wherein N-acetylneuraminic acid is bound

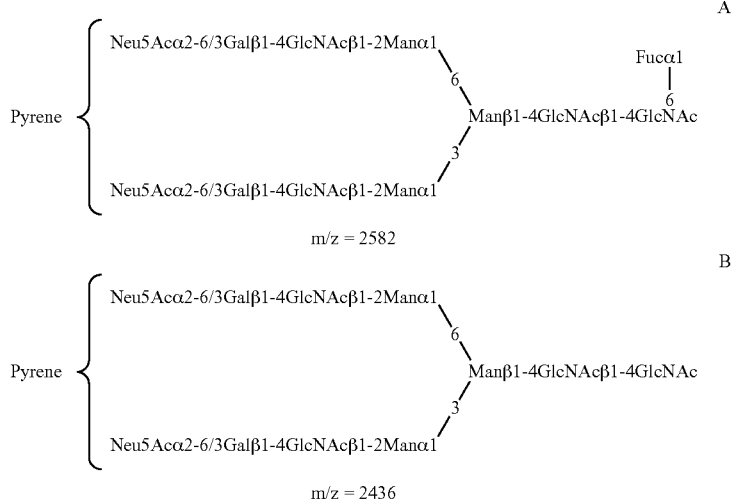

Figure 2:
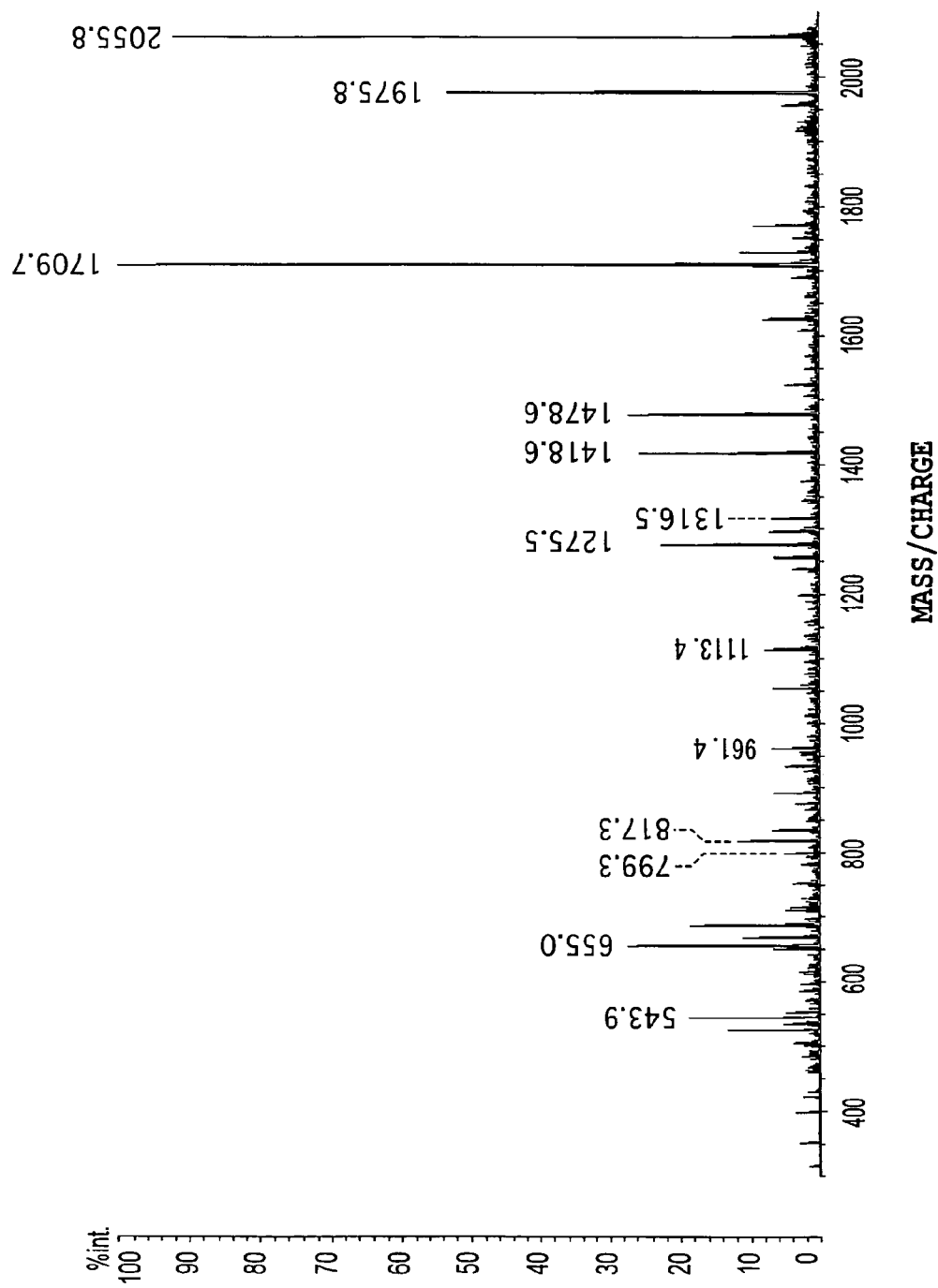
FIG. 2 is a diagram showing the negative ion $MS^2$ spectrum obtained in Example 1, wherein the peak $P_{2A}$ of m/z=2077 was used as the precursor ion.

FIG. 2 shows the MS² spectrum obtained by using the peak $P_{2A}$ of m/z=2077 in FIG. 1 as a precursor ion. It was deduced that the ions in the peak Pa have a diantennary structure, wherein one N-acetylneuraminic acid and one fucose are bound. Furthermore, based on the following discussion, the positions where they are attached were determined. In the spectrum of FIG. 2, although the peak of m/z=1709, corresponding to the branch structure at the side of the 6-position of Man. In addition, by detecting a group of the peaks of m/z=1316, m/z=1113, m/z=799 and the like, it was revealed that the isomer, wherein N-acetylneuraminic acid is α2-6 bound (the structure represented by Formula C), and the isomer, wherein N-acetylneuraminic acid is α2-3 bound (the structure represented by Formula D), are mixed.

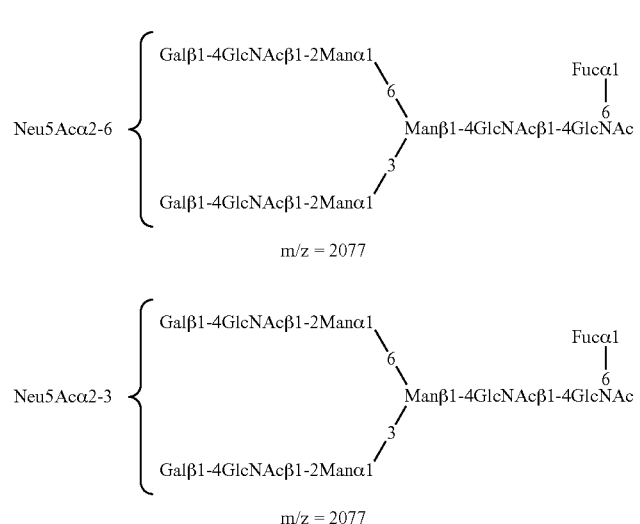

-continued

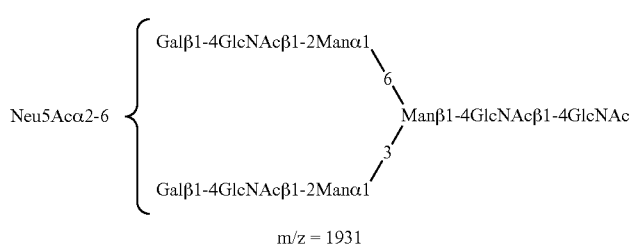

E m/z = 1931

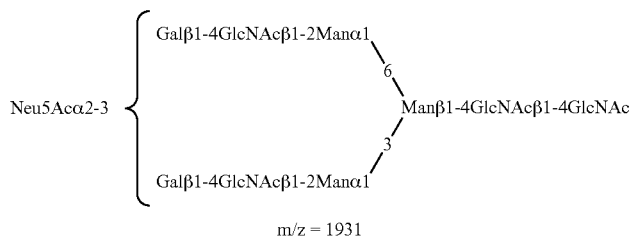

F m/z = 1931

Figure 3:
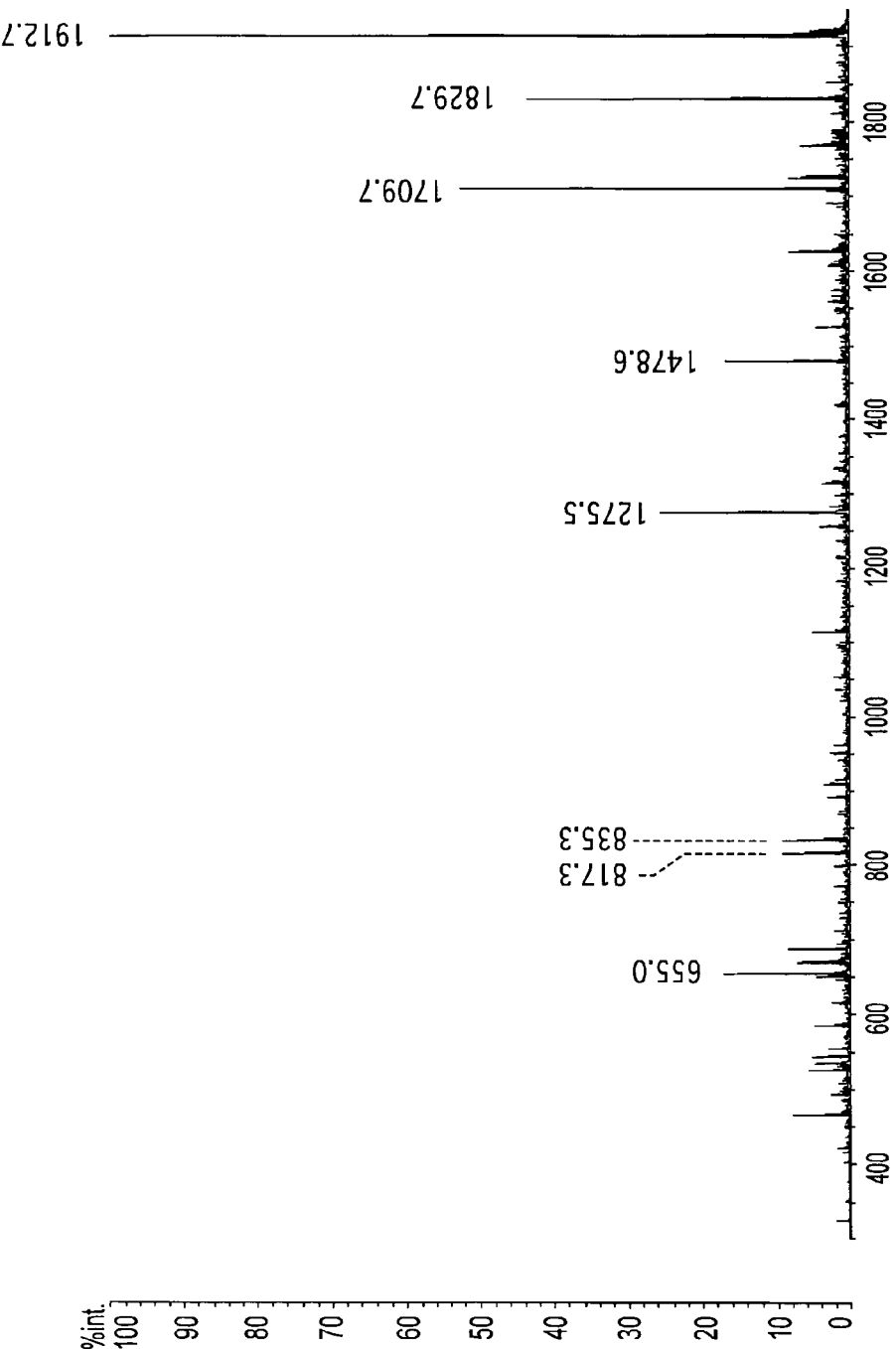
FIG. 3 is a diagram showing the negative ion $MS^2$ spectrum obtained in Example 1, wherein the peak $P_{2B}$ of m/z=1931 was used as the precursor ion.

FIG. 3 shows the MS² spectrum obtained by using the peak $P_{2B}$ of m/z=1931 in FIG. 1 as a precursor ion. It was deduced that the ions in the peak $P_{2B}$ have a diantennary structure, which does no have fucose and is bound by one N-acetylneuraminic acid. Since the peak of m/z=961, which corresponds to Neu5Ac-Gal-GlcNAc-Man-Man, which is ion D, was not detected virtually, it was found that the predominat isomers are the ones wherein N-acetylneuraminic acid is bound to the branch structure at the side of the 3-position of Man. Moreover, since the peak of m/z=835 was markedly detected instead of a group of peaks of m/z=1316, m/z=799 and the like, it has been revealed that the predominant isomers are the one wherein N-acetylneuraminic acid is α2-3 bound (the structure represented by Formula F), and the one wherein N-acetylneuraminic acid is α2-6 bound (the structure represented by Formula E).

In addition, the structure in which a Gal residue is substituted by an N-acetyl galactosamine (GalNAc) residue was detected as well as the structures represented by Formulae A through F.

As described above, by the method of the present invention, the detailed structures of glycans of serum PSA derived from a BPH patient was first revealed.

Examples 2 through 16

The procedure of Example 1 was repeated by using sera of 3 subjects, who have been diagnosed with BPH, anonymised, and added with identification codes (Examples 2 through 4), as well as sera of 12 subjects, who have been diagnosed with PC by biopsy, anonymised, and added with identification codes (Examples 5 through 16). Moreover, the study underwent ethics review at a medical institution and was approved. The subjects were informed, and the consent was given from the subjects.

The following Table 1 shows PSA concentration in serum and the signal intensity ratio R of fucose-unbound glycan (m/z=2436)/fucose-bound glycan (m/z=2582) in each subject. Moreover, the signal intensity ratio of fucose-unbound glycan (m/z=1931)/fucose-bound glycan (m/z=2077), wherein the pyrene-labeled portion and one N-acetylneuraminic acid residue were eliminated, showed a similar R value.

TABLE 1

Evaluation results of Examples 1 through 16

| | Identification code | Disease name | PSA concentration in serum (ng/mL) | R |
|---|---|---|---|---|
| Example 1 | T-13 | BPH | 112.6 | 0.69 |
| Example 2 | N-9 | BPH | 34.7 | 1.00 |
| Example 3 | N-10 | BPH | 36.3 | 0.79 |
| Example 4 | T-16 | BPH | 40.4 | 0.75 |
| Example 5 | N-52 | PC | 18.2 | 1.60 |
| Example 6 | N-32 | PC | 26.3 | 2.30 |
| Example 7 | N-27 | PC | 30.3 | 3.20 |
| Example 8 | N-28 | PC | 30.6 | 13.30 |
| Example 9 | T-10 | PC | 36.4 | 6.89 |
| Example 10 | N-41 | PC | 40.4 | 5.20 |
| Example 11 | N-14 | PC | 54.2 | 1.30 |
| Example 12 | N-23 | PC | 60.4 | 2.80 |
| Example 13 | N-24 | PC | 66.0 | 6.10 |
| Example 14 | T-31 | PC | 101.5 | 1.87 |
| Example 15 | T-11 | PC | 141.8 | 5.72 |
| Example 16 | N-17 | PC | 1140.0 | 3.13 |

Figure 4:
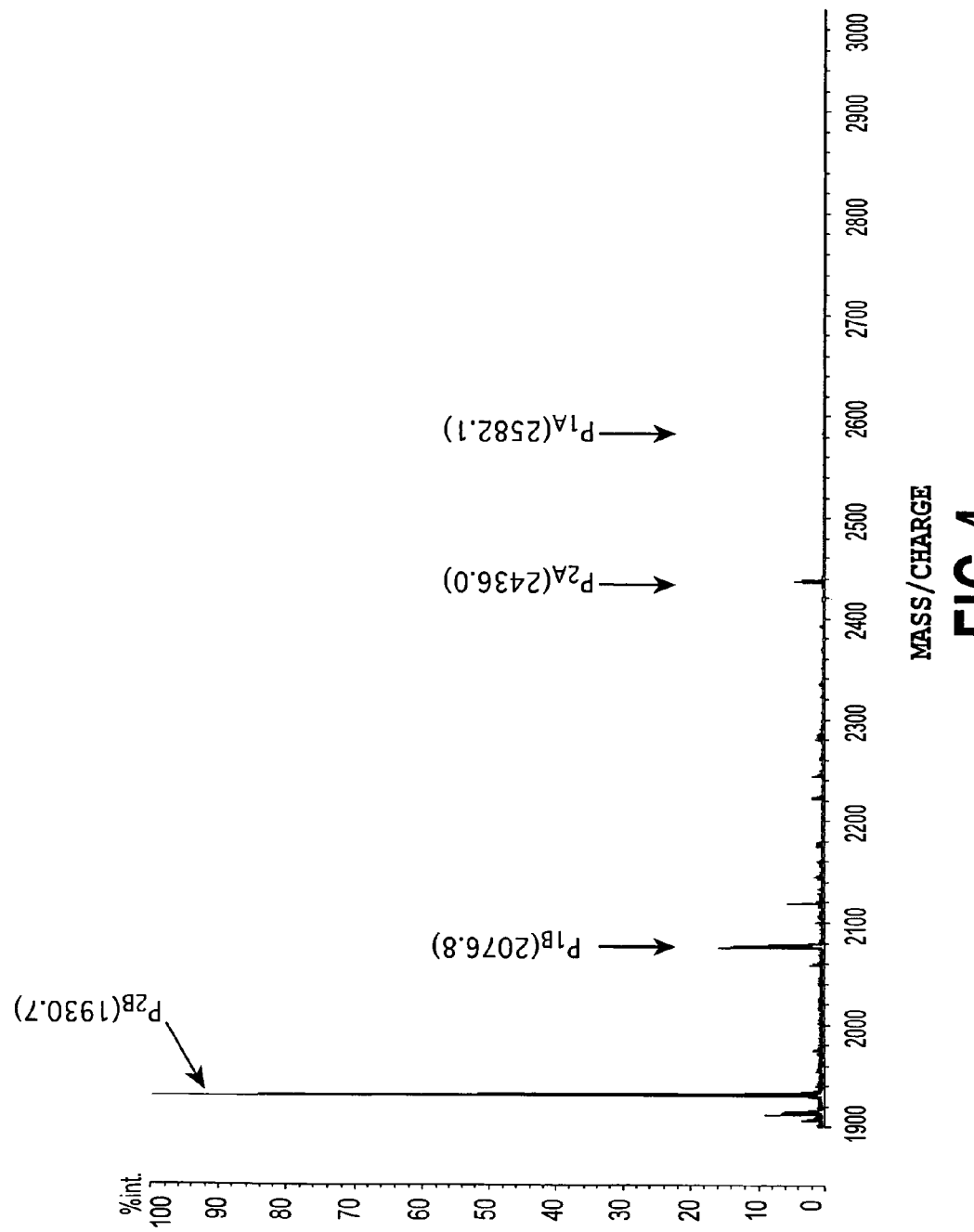
FIG. 4 is a diagram showing the negative ion MS spectrum obtained in Example 15.

As a representative example in which serum of a subject who has been diagnosed with PC, FIG. 4 shows the MS spectrum obtained in Example 15 in which serum having a similar level of PSA concentration in serum to the serum used in Example 1 was used. MS² analysis by the same procedure as Example 1 confirmed the presence of the glycans having the structures represented by Formulae A through F also in Example 15.

In addition, the structures in which a Gal residue is substituted by a GalNAc residue were detected as well as the structures represented by Formulae A through F. Moreover, from the sera of the subjects who have been diagnosed with PC, highly branched triantennary and tetraantennary glycans were detected in addition to biantennary glycans. Furthermore, the structure in which a Gal residue is substituted by a GalNAc residue was detected in any one of the biantennary, triantennary and tetrantennary glycans.

(Evaluation)

As shown in Table 1, it is found that the samples derived from the sera of the subjects who have been diagnosed with PC showed the signal intensity ratio R of fucose-unbound glycan/fucose-bound glycan greater than 1.0, and thus they contained a large amount of fucose-unbound glycans. In contrast, the signal intensity ratio R of the samples derived from the sera of the subjects who have been diagnosed with BPH was 1.0 or less. More specifically, it was first revealed that the sera of subjects who were diagnosed with BPH contain more fucose-bound glycans than fucose-unbound glycans.

Moreover, as it is obvious from the comparison of Examples 2 through 4 and 9 through 10, as well as the comparison of Example 1 and Example 14, even in samples having almost the same level of PSA concentration in serum, it was found that the relationship between the amounts of fucose-unbound glycans and fucose-bound glycans was totally different in the case of PC and in the case of BPH.

Furthermore, it was found that the signal intensity ratio R of fucose-unbound glycan/fucose-bound glycan, surprisingly, has no correlation with serum PSA concentration in both PC and BPH. This result indicates that the method of the present invention can accurately discriminate between PC and BPH without depending on PSA concentration. Therefore, the method of the present invention can be applied to samples whose PSA concentration in serum is in the range of 1 to 1200 ng/mL, preferably 1 to 100 ng/mL, and more preferably 4 to 50 ng/mL. In particular, the method of the present invention is effective in accurately discriminating between PC and BPH even for PSA concentration in serum in the range of the so-called gray zone (4 to 10 ng/mL).

Example 17

The present example is an example which shows a glycopeptides can be used instead of glycans in the above described examples.

By using a reference standard PSA (Nippon Chemi-Con Corp.), electrophoresis at the fifth stage described in step 1 of Example 1 and the steps of reduction with DTT, alkylation with iodoacetamide, rinsing and drying described in step 2 were performed to obtain a dried gel. In this case, reduction with DTT and alkylation with iodoacetamide described in step 2 may not be performed.

Next, to the dried gel, an aqueous solution of 25 mM ammonium bicarbonate of 1 to 100 units of thermolysin (Calbiochem) (pH 8.0) was added, and the mixture was left to stand in an ice bath for 45 minutes to swell the gel. The swollen gel was gently agitated for 18 hours at 56° C. To the gel, an extraction solution (an aqueous solution containing 70 to 80% acetonitrile and 0.1% trifluoroacetic acid) was added, shaken for 20 minutes, and the solution was collected.

The collected solution was added to 25 mg of rinsed ZIC (registered trademark) HILIC solid phase column filler (Merck SeQuant AB). Subsequently, an aqueous solution containing 80% acetonitrile and 0.1% trifluoroacetic acid was added and rinsed, and an aqueous solution of 0.1% trifluoroacetic acid was used to elute a glycopeptide. The glycopeptide eluate was dried on a centrifugal concentrator, and the solid residue was then dissolved in 2 μL of purified water to obtain a glycopeptide solution.

Figure 5:
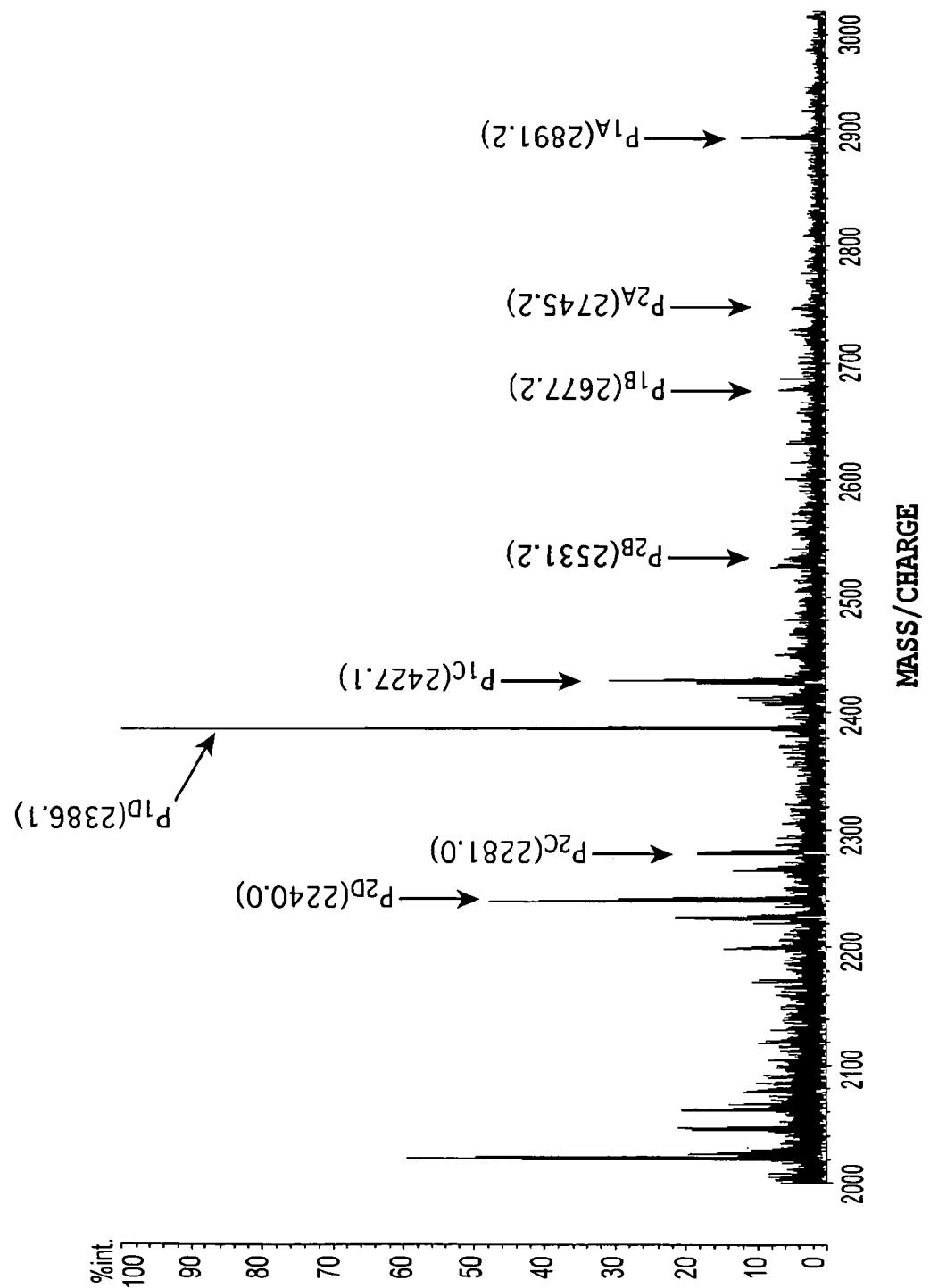
FIG. 5 is a diagram showing the positive ion MS spectrum obtained in Example 17.

By applying the same procedure as step 3 of Example 1 to the obtained glycopeptide solution, labeling of the glycopeptides was performed. Next, by applying the procedure of step 4 of Example 1 to the obtained target plate, an MS analysis was performed. By MS analysis, glycopeptides, wherein glycans are bound to peptides 43 through 47 derived from PSA, were detected. FIG. 5 shows the obtained MS spectrum. As shown in FIG. 5, 4 pairs of fucose-bound glycopeptide ($P_1$) and fucose-unbound glycopeptide ($P_2$), whose molecular weights differ by 146 Da corresponding to the presence or absence of fucose, were found.

$P_{1A}(m/z=2891.2)/P_{2A}(m/z=2745.2)$ $P_{1B}(m/z=2677.2)/P_{2B}(m/z=2531.2)$ $P_{1C}(m/z=2427.1)/P_{2C}(m/z=2281.0)$ $P_{1D}(m/z=2386.1)/P_{2D}(m/z=2240.0)$

In any of the pairs, the signal intensity ratio R' of fucose-unbound glycopeptide/fucose-bound glycopeptide was 1.0 or less. Moreover, to the reference standard PSA used in the present example, glycan structures were analyzed by applying electrophoresis at the fifth stage described in step 1 of Example 1 and the same procedure as steps 2 through 4. The obtained signal intensity ratio R of fucose-unbound glycan/fucose-bound glycan was 1.0 or less.

As described above, even when the glycopeptide was used as a PSA derivative, a pair of peaks of fucose-unbound glycopeptide and fucose-bound glycopeptide, whose molecular weights differ by 146 Da corresponding to the presence or absence of fucose, could be detected in MS analysis after labeling. Furthermore, the signal intensity ratio R' of the pair of glycopeptides showed the same results as the signal intensity ratio R of the pair of glycans. Therefore, similarly to the signal intensity ratio R of fucose-unbound glycan/fucose-bound glycan shown in Examples 1 through 16, it is considered that PC and BPH can be accurately discriminated by calculating the signal intensity ratio R' of fucose-unbound glycopeptide/fucose-bound glycopeptide.

Moreover, when the glycopeptide is used, since the peptide is bound to glycans, it is made possible to identify PSA and confirm the positions where the glycans are attached. This enables an accurate calculation of the signal intensity ratio R' of fucose-unbound glycopeptide/fucose-bound glycopeptide even when other glycoproteins are mixed.

Example 18

The procedure of Example 9 was repeated except that a buffer containing 200 ng endoproteinase Arg-C (Roche Diagnostics K.K.) (containing 50 mM Tris-HCl, pH 7.6, 5 mM DTT and 0.5 mM EDTA) was used instead of an aqueous solution of ammonium bicarbonate of thermolysin, and the reaction temperature for the digestion in the gel was changed to 37° C.

On MS analysis, the glycopeptides, wherein glycans are bound to peptides 45 through 53 derived from PSA, were detected. Similarly to Example 17, some pairs of peaks of fucose-unbound glycopeptides/fucose-bound glycopeptides, whose molecular weights differ by 146 Da corresponding to the presence or absence of fucose, was detected.

Example 19

From sera of patients suffering from BPH or PC, glycopeptides can be prepared by purifying PSA by performing step 1 in accordance with Example 1 and then performing step 2 in accordance with the procedure of Example 17 or 18. Furthermore, by performing steps 3 and 4 in accordance with the procedure of Example 17 or 18, a pair of peaks of fucose-unbound glycopeptide/fucose-bound glycopeptide, whose molecular weights differ by 146 Da corresponding to the presence or absence of fucose, can be detected.

Example 20

Figure 6:
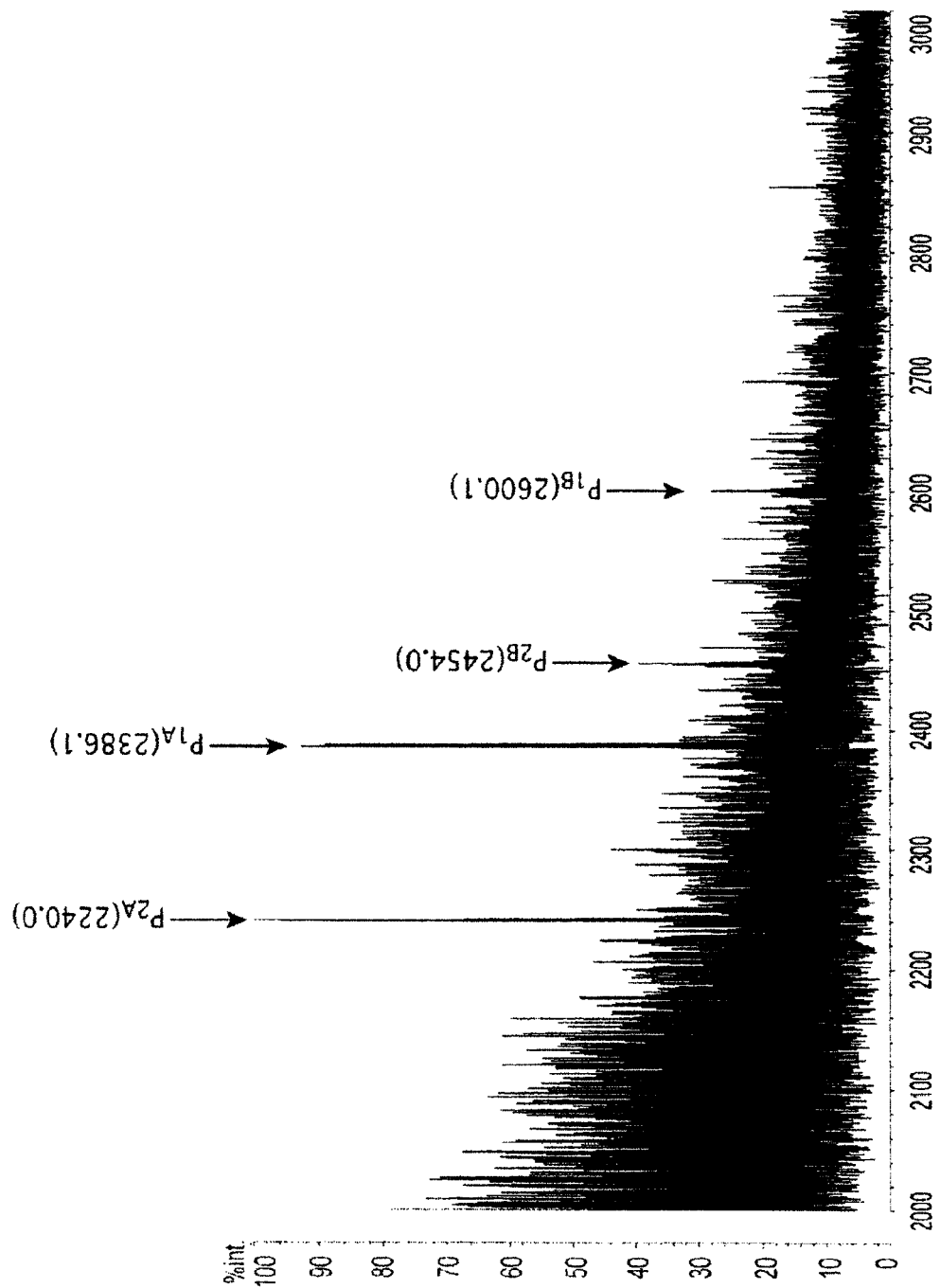
FIG. 6 is a diagram showing the positive ion MS spectrum obtained in Example 20.

By using serum of a patient actually suffering from PC (N-46, PSA concentration 1.6 μg/mL), thermolysin treatment was performed in the gel in accordance with the procedure in Example 17. The gel extraction solution was dried on a centrifugal concentrator. The obtained solid residue was dissolved in an aqueous solution of 0.8% trifluoroacetic acid, and the mixture was left to stand for 30 minutes at 80° C. to perform a desialation reaction. The desialated sample was dried on a centrifugal concentrator. The obtained solid residue was dissolved in an aqueous solution containing 5% acetonitrile and 0.1% trifluoroacetic acid. By using a C18 chip filled with octadecyl (C18) silica, suction and ejection of the reaction mixture were repeated. As a result, the peptides were adsorbed, and a glycopeptide fraction was obtained. To the obtained glycopeptide fraction, acetonitrile was added so that a final concentration of acetonitrile was adjusted to 80%. Purification by ZIC (registered trademark) HILIC solid phase column filler (Merck SeQuant AB), and the subsequent steps 3 and 4 were performed similarly to Example 17. FIG. 6 shows the obtained MS spectrum as a result. The value of the signal intensity ratio of fucose-unbound glycopeptide/fucose-bound glycopeptides was certainly shown to be greater than 1.0. This result was consistent with the result of glycan analysis.

Example 21

Without performing PSA isolation described in step 1 and the steps of reduction with DTT and alkylation with iodoacetamide described in step 2 of Example 1, to 50 ng of commercially available PSA (Nippon Chemi-Con Corp.) or 50 ng of PSA-ACT complex (Cortex Biochem, Inc.), an aqueous solution of 25 mM ammonium bicarbonate (pH 8.0) of 10 units of thermolysin (Calbiochem) was directly added, and the mixture was reacted while left to stand for 18 hours at 56° C.

The thermolysin-digested solution was dried on a centrifugal concentrator. The obtained solid residue was dissolved in an aqueous solution of 0.8% trifluoroacetic acid, and the mixture was left to stand for 30 minutes at 80° C. to perform a desialylation reaction. The desialylated sample was dried on a centrifugal concentrator. The obtained solid residue was dissolved in an aqueous solution containing 5% acetonitrile and 0.1% trifluoroacetic acid. By using a C18 chip filled with octadecyl (C18) silica, suction and ejection of the reaction mixture were repeated. As a result, the peptides were adsorbed and separated from glycopeptides in the reaction mixture to obtain a glycopeptide fraction. To the obtained glycopeptide fraction, acetonitrile was added so that a final concentration of acetonitrile was adjusted to 80%. To 25 mg of rinsed ZIC (registered trademark) HILIC solid phase column filler (Merck SeQuant AB), the glycopeptide fraction was added. Subsequently, it was rinsed by adding an aqueous solution containing 80% acetonitrile and 0.1% trifluoroacetic acid, and the glycopeptides were eluted with an aqueous solution of 0.1% trifluoroacetic acid. The glycopeptide eluate was dried on a centrifugal concentrator, and the solid residue was then dissolved in 2 μL of purified water to obtain a glycopeptide solution.

Figure 7A:
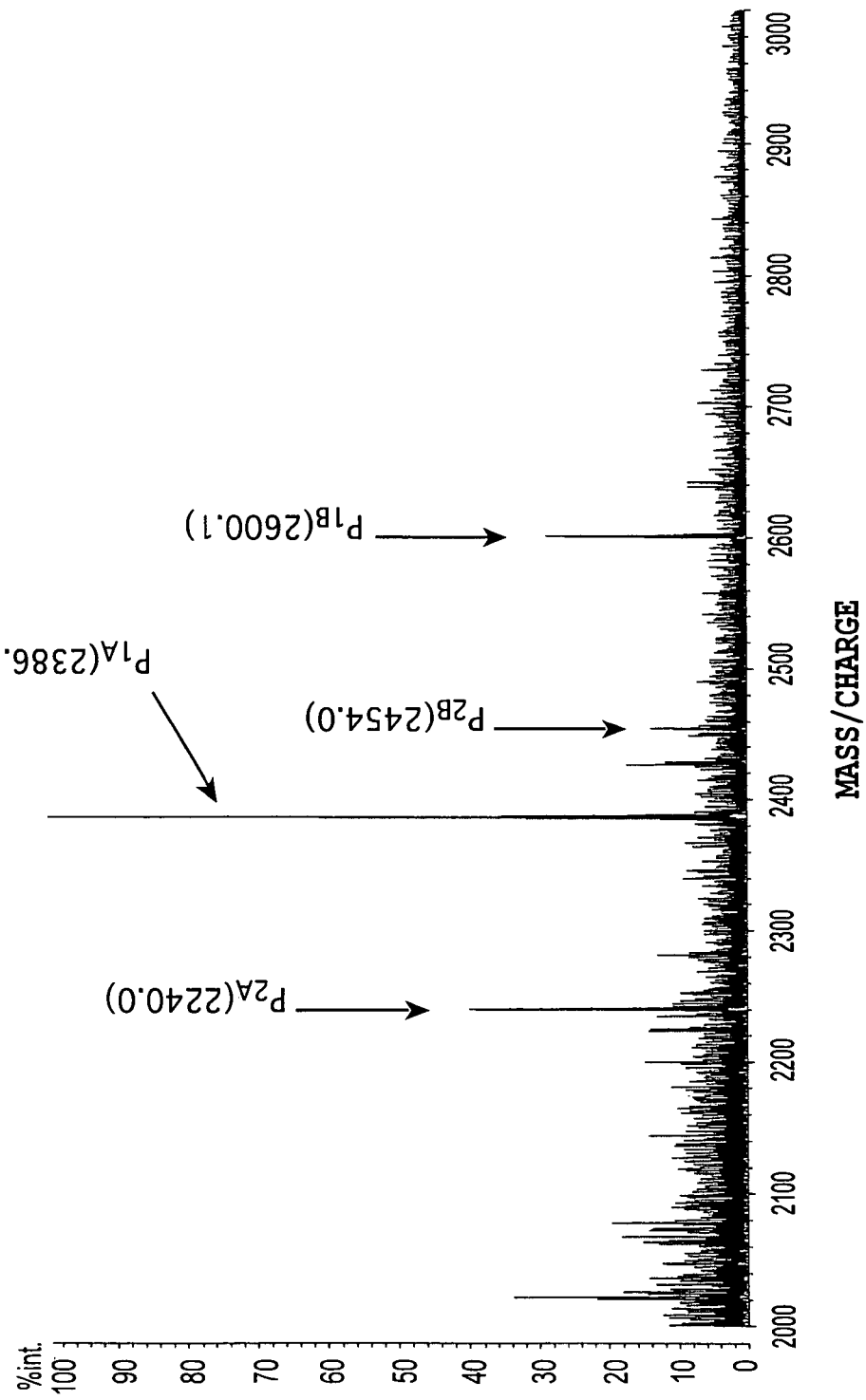
FIG. 7A is a diagram showing the positive ion MS spectrum of the glycopeptide derived from PSA obtained in Example 21.
Figure 7B:
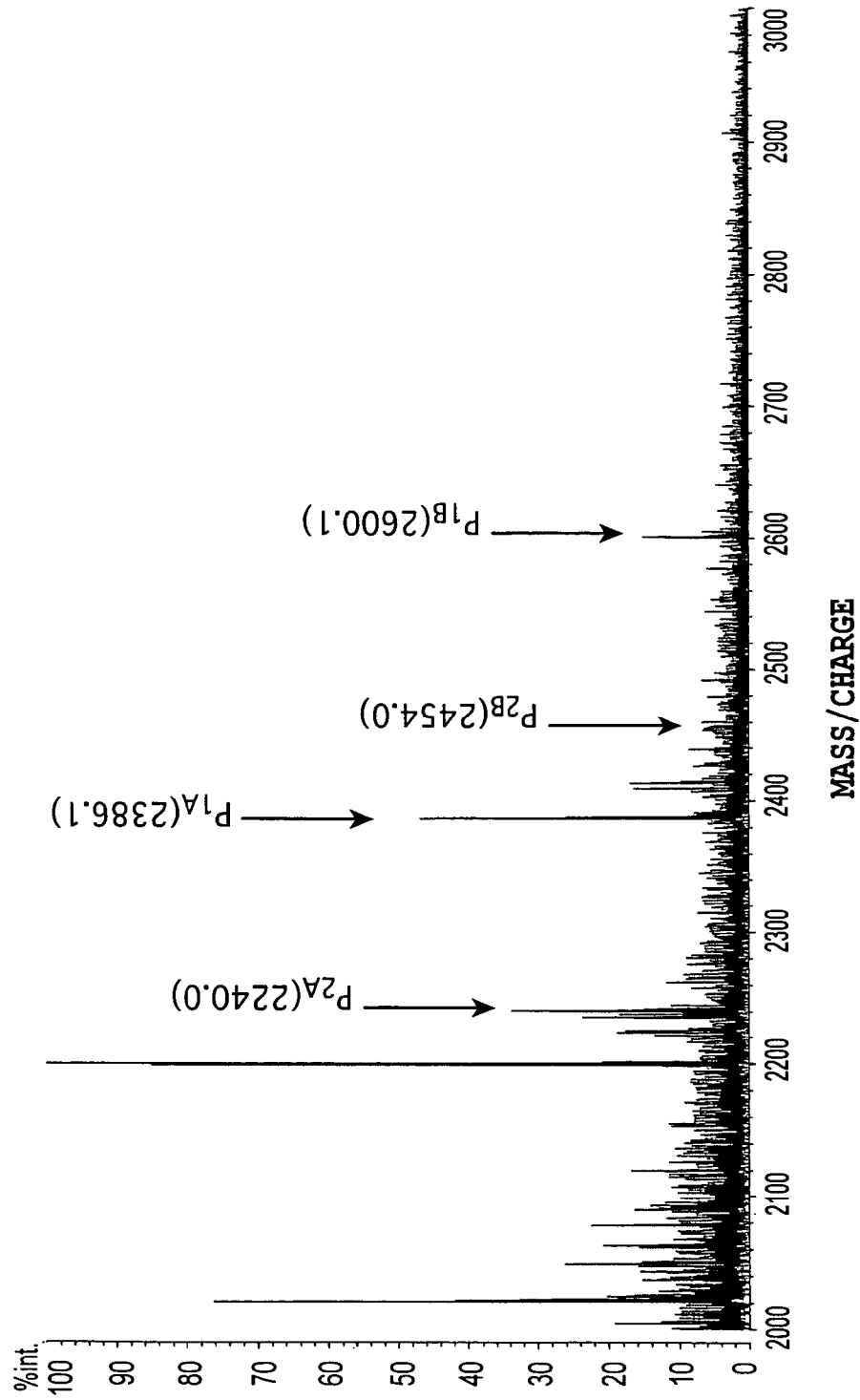
FIG. 7B is a diagram showing the positive ion MS spectrum of the glycopeptide derived from PSA-ACT complex obtained in Example 21.

The same procedure as step 3 in Example 1 was applied to the obtained glycopeptide solution to perform labeling of the glycopeptides. Next, the procedure of step 4 of Example 1 was applied to the obtained target plate to perform an MS analysis. On MS analysis, glycopeptides, wherein glycans are bound to peptides 43 through 47 derived from PSA, were similarly detected from PSA and PSA-ACT complex. FIG. 7A and FIG. 7B show the obtained MS spectrum. FIG. 7A is a diagram showing the MS spectrum of the glycopeptides derived from PSA, and FIG. 7B is a diagram showing the MS spectrum of the glycopeptides derived from PSA-ACT complex. As shown in FIG. 7A and FIG. 7B, two pairs of fucose-bound glycopeptides ($P_1$) and fucose-unbound glycopeptides ($P_2$), whose molecular weights differ by 146 Da corresponding to the presence or absence of fucose, were detected.

$$P_{1A}(m/z=2386.1)/P_{2A}(m/z=2240.0)$$

$$P_{1B}(m/z=2600.1)/P_{2B}(m/z=2454.0)$$

As described above, without preparing free PSA from PSA-ACT complex as done in Example 1, the glycopeptides were directly prepared from the complex, and the fucose-bound glycopeptides and fucose-unbound glycopeptides of PSA could be detected. This method is simple and rapid because it has fewer steps and, moreover, improves the recovery rate of glycopeptide. Therefore, it is preferred to apply this method to clinical samples.

Example 22

The present example is an example of performing an analysis of a patient's serum without performing PSA isolation described in step 1 and the steps of reduction with DTT and alkylation with iodoacetamide described in step 2 of Example 1, similarly to Example 21.

First, immunoglobulin was removed from serum of a patient suffering from PC(N-99, PSA concentration 90.3 ng/mL). Three mL of Protein A agarose carrier (Pierce Biotechnology, Inc.) was equilibrated by using. PBS. This was filled into a disposable plastic column (Pierce Biotechnology, Inc.), and the mixture of the serum of the subject (N-99) and PBS was added thereto. The column was shaken for 30 minutes at 4° C. A fraction containing PSA which was not bound to the carrier was collected. Furthermore, the separated Protein A agarose carrier was rinsed with 3 column volume (3 CV) of PBS, and the rinsing solution was combined to the fraction containing PSA. To the fraction containing PSA, $Na_2SO_4$ was added to a final concentration of 1 M.

Next, albumin, which is a major protein in serum, was removed from the fraction containing PSA. A disposable plastic column was filled with 2.5 mL of Fractogel (trademark) EMD TA(S) (Merck KGaA), and equilibrated with 20 mM phosphate buffer (pH 7.4, containing $Na_2SO_4$ (1 M)). The obtained fraction by the above described method was added to the Fractogel (trademark)-filled column, and 7 CV of the same buffer was pumped to the column by using a liquid feed pump to discharge albumin. Next, the adsorbed protein was eluted from the Fractogel (trademark)-filled column with 20 mM phosphate buffer (pH 7.4, not containing $Na_2SO_4$) to obtain a fraction containing PSA.

Next, the fraction was added to 2 mL of Protein A agarose carrier equilibrated by using PBS, and shaked for 30 minutes at 4° C. to further remove immunoglobulin. A fraction containing PSA which was not bound to Protein A agarose carrier was collected. Moreover, the separated Protein A agarose carrier was rinsed with 3 column volume (3 CV) of PBS, and the rinsing solution was combined to the fraction containing PSA. The obtained fraction was used for the next immunoprecipitation.

Subsequently, anti-PSA antibody beads to be used for immunoprecipitation were prepared. NHS-activated Sepharose 4 Fast Flow (GE Healthcare. Bio-Sciences Ltd.) was rinsed three times with 1 mM HCl. Next, to the beads after rinsing, a commercially available anti-human PSA rabbit polyclonal antibody (manufactured by DAKO Inc.) was added. The mixture was shaken for 30 minutes at room temperature to perform crosslinking between the antibody and the beads. Subsequently, 0.5 M monoethanolamine solution containing 0.5 M NaCl was added, and the mixture was shaken for 30 minutes to perform masking of the residual active groups. The obtained anti-PSA antibody beads were rinsed three times alternately with 0.1 M sodium acetate buffer (pH 4.0) containing 0.5 M NaCl and 0.1 M Tris buffer (pH 9.0) containing 0.5 M NaCl. Subsequently, the anti-PSA antibody beads were rinsed three times with PBS. Finally, the anti-PSA antibody beads were rinsed with PBS containing 0.02% sodium azide, and stored at 4° C. until use.

Next, immunoprecipitation was performed. To the above described fraction containing PSA, wherein albumin and globulin were removed, 0.1 ml of the anti-PSA antibody beads was added, and shaken for 1 hour at 4° C. Subsequently, the anti-PSA antibody beads were transferred to a Micro Bio-Spin chromatography column (Bio-Rad Laboratories, Inc.). The anti-PSA antibody beads column was rinsed four times with PBS, three times with PBS containing 0.02% Tween-20 and twice with distilled water. Moreover, 1 M propionic acid was added to the anti-PSA antibody beads column to elute and collect the protein adsorbed to the antibody beads. Elution with 1 M propionic acid was repeated 10 times, and the combined eluate was dried on a centrifugal concentrator(SpeedVac (SAVANT)).

As a result of analyzing the dried protein by the Enzyme-Linked ImmunoSorbent Assay method (ELISA, Eiken Chemical Co., Ltd.) and electrophoresis, it was revealed that approximately 70% of PSA contained in the initial serum could be collected. The above process can be completed within 2 days and, therefore, is a simple and rapid process with high yield.

Next, enzymatic digestion of the protein with thermolysin was performed. The dried protein was dissolved in an aqueous solution of 50 mM ammonium bicarbonate (pH 8.0), and 50 units of thermolysin (Calbiochem) was added. The mixture was left to stand for 18 hours at 56° C. The reaction mixture was dried on a centrifugal concentrator. The obtained solid residue was dissolved in an aqueous solution of 0.8% trifluoroacetic acid, and the mixture was left to stand for 40 minutes at 80° C. to perform a desialylation reaction. The desialylated sample was dried on a centrifugal concentrator to obtain a glycopeptide fraction.

Subsequently, by using 50 mg of Intersep GC, which is a carbon graphite-filled cartridge (GL Sciences Inc.), crude purification and desalting of the obtained glycopeptide fraction were performed. First, to the cartridge, an aqueous solution of 1 M NaOH, distilled water, an aqueous solution of 30% acetic acid, distilled water, an aqueous solution containing 80% acetonitrile and 0.1% trifluoroacetic acid, and an aqueous solution containing 5% acetonitrile and 0.1% trifluoroacetic acid were sequentially pumped to perform rinsing and equilibration of the filled carbon graphite. Next, the dried glycopeptide fraction was dissolved in an aqueous solution containing 5% acetonitrile and 0.1% trifluoroacetic acid and pumped to the cartridge. To the cartridge, wherein the glycopeptide fraction was adsorbed, distilled water and an aqueous solution containing 5% acetonitrile and 0.1% trifluoroacetic acid were subsequently pumped to perform crude purification and desalting of the glycopeptide fraction. Subsequently, to the cartridge, an aqueous solution containing 80% acetonitrile and 0.1% trifluoroacetic acid was pumped to elute the adsorbed glycopeptides. The eluate containing the glycopeptides was collected and dried on a centrifugal concentrator.

By using Sepharose CL-4B (SIGMA-ALDRICH Corp.), purification of the glycopeptides was performed. Before use, Sepharose was rinsed five times with an aqueous solution of 50% ethanol and then rinsed five times with a mixed solution of butanol:distilled water:ethanol=4:1:1. The dried crude purified glycopeptide fraction was dissolved in the same mixed solution. To the solution, 6 μL of the rinsed Sepharose was added, and shaken for 1 hour at room temperature to allow the glycopeptides adsorbed on Sepharose. Subsequently, by using the above described mixed solution, Sepharose was rinsed nine times. To Sepharose on which the glycopeptides were adsorbed, an aqueous solution of 50% ethanol was added, and shaken for 30 minutes at room temperature to elute the glycopeptides. A solution containing the eluted glycopeptides was collected, and dried on a centrifugal concentrator. Subsequently, the obtained solid residue was dissolved in 4 μL of an aqueous solution of 5% acetonitrile.

Figure 8:
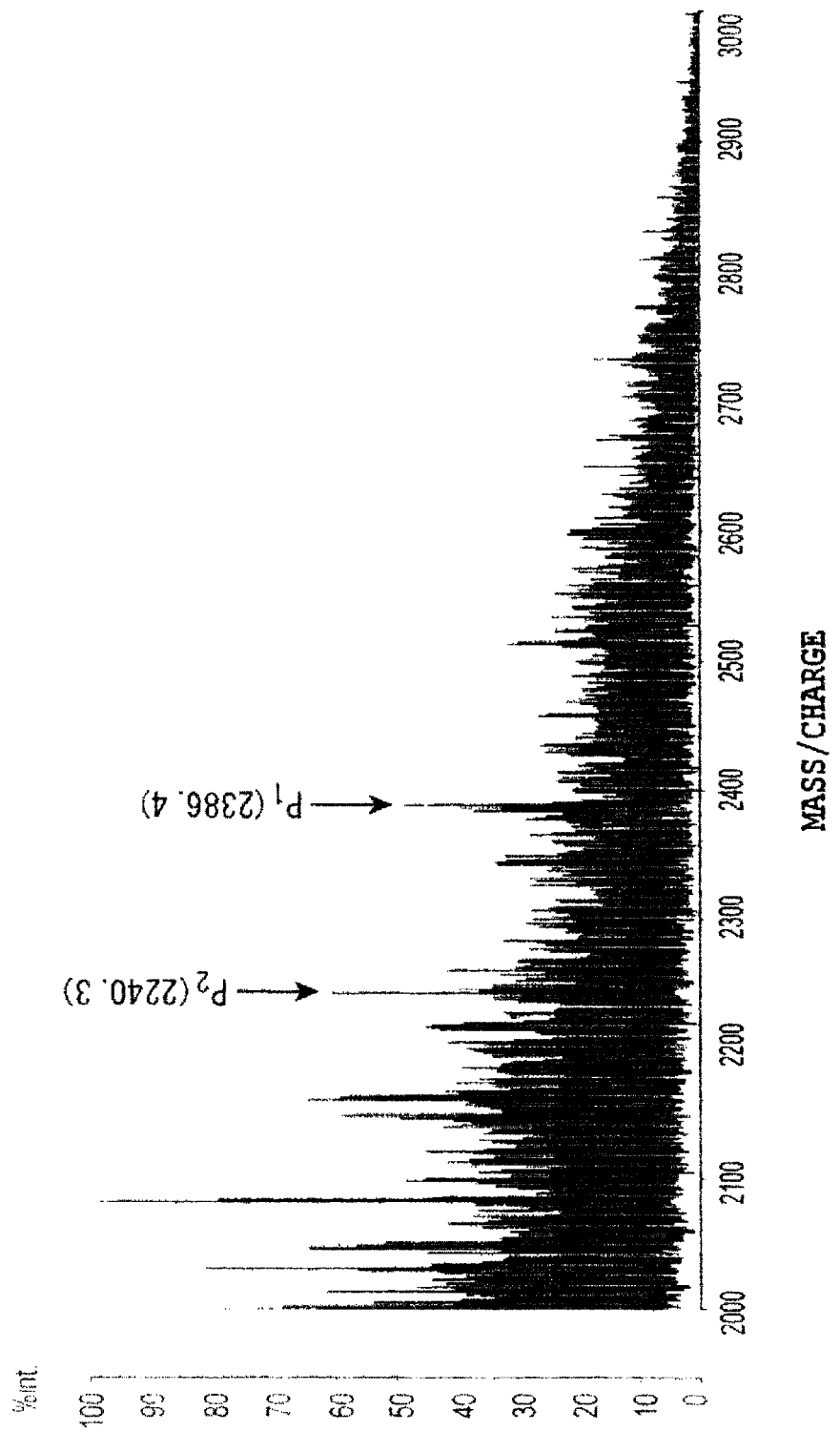
FIG. 8 is a diagram showing the positive ion MS spectrum obtained in Example 22.

The same procedure as step 3 in Example 1 was applied to the obtained glycopeptide solution to perform labeling of the glycopeptides. Next, the procedure of step 4 of Example 1 was applied to the obtained target plate to perform an MS analysis. By MS analysis, glycopeptides, wherein glycans are bound to peptides 43 through 47 derived from PSA, were certainly detected. FIG. 8 shows the obtained MS spectrum. Two fucose-bound glycopeptide ($P_1$) and fucose-unbound glycopeptide ($P_2$), having molecular weights of 146 Da corresponding to the presence or absence of fucose, were detected.

$$P_1(m/z=2386.4)/P_2(m/z=2240.3)$$

The signal intensity ratio R of fucose-unbound glycopeptide (m/z=2240.3)/fucose-bound glycopeptide (m/z=2386.4) on PSA in serum of the subject was 1.23.

As described above, detection of the glycopeptides from serum of a patient with prostate carcinoma, which has a low PSA concentration of 90.3 ng/mL, was successfully conducted by MS for the first time. Moreover, it was revealed that the signal intensity ratio of fucose-unbound glycan/fucose-bound glycan was greater than 1.0 even in PSA in serum of a patient with prostate carcinoma, which has a low PSA concentration, similarly to PSA in serum of a patient with prostate carcinoma, which has a high PSA concentration of 1000 ng/ml or more.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A method for discriminating between prostate carcinoma and benign prostatic hyperplasia, comprising the steps of:
    (1) purifying prostate specific antigen (PSA) PSA from a sample derived from a subject;
    (2) preparing a PSA derivative from the PSA purified in Step (1);
    (3) labeling the PSA derivative obtained in Step (2);
    (4) analyzing the labeled PSA derivative obtained in Step (3) by a mass spectrometry method; and
    (5) determining a ratio of a signal intensity of fucose-unbound glycan to a signal intensity of fucose-bound glycan in the labeled PSA derivative,
    wherein the subject is identified as having prostate carcinoma when the ratio is greater than 1.0, and identified as having benign prostatic hyperplasia when the ratio is 1.0 or less.

2. The method according to claim 1, wherein the PSA derivative prepared in Step (2) is a glycan derived from PSA.

3. The method according to claim 1, wherein the PSA derivative prepared in Step (2) is a glycopeptide derived from PSA.

* * * * *